United States Patent
Bae et al.

(10) Patent No.: US 12,026,873 B2
(45) Date of Patent: Jul. 2, 2024

(54) BONE AGE ASSESSMENT METHOD FOR BONE IMAGE

(71) Applicant: VUNO Inc., Seoul (KR)

(72) Inventors: Byeonguk Bae, Incheon (KR); Kyuhwan Jung, Seoul (KR)

(73) Assignee: VUNO Inc., Seoul (KR)

( * ) Notice: Subject to any disclaimer, the term of this patent is extended or adjusted under 35 U.S.C. 154(b) by 475 days.

(21) Appl. No.: 17/354,861

(22) Filed: Jun. 22, 2021

(65) Prior Publication Data

US 2021/0398280 A1    Dec. 23, 2021

(30) Foreign Application Priority Data

Jun. 23, 2020    (KR) .................. 10-2020-0076520
Jul. 24, 2020    (KR) .................. 10-2020-0092344

(51) Int. Cl.
*G06T 7/00*        (2017.01)
*G06N 3/047*       (2023.01)
(Continued)

(52) U.S. Cl.
CPC .......... *G06T 7/0012* (2013.01); *G06N 3/047* (2023.01); *G16H 50/20* (2018.01); *G16H 50/30* (2018.01);
(Continued)

(58) Field of Classification Search
CPC ......... G06T 7/0012; G06T 2207/20081; G06T 2207/20084; G06T 2207/20182;
(Continued)

(56) References Cited

U.S. PATENT DOCUMENTS 6,213,934 B1 *  4/2001  Bianco .................. A61B 5/417
                                                   600/14
11,735,322 B2 *  8/2023  Zhang ................... G16H 50/50
                                                   382/128
(Continued)

FOREIGN PATENT DOCUMENTS

EP       3696727 A1       8/2020
KR    10-2019-0023003 A   3/2019
KR       10-1977174 B1    5/2019

OTHER PUBLICATIONS

Liu et al, Bone Age Assessment by Deep convolutional Neural Networks combined with Clinical TW3-RUS, 2019, IEEE 2019 International Conference on Bioinformatics and Biomedicine, pp. 949-952 (Year: 2019).*

(Continued)

*Primary Examiner* — Lewis G West
(74) *Attorney, Agent, or Firm* — Seed IP Law Group LLP

(57) ABSTRACT

According to an embodiment of the present disclosure, a computer program stored in a computer readable storage medium is disclosed. The computer program includes instructions for causing one or more processors to estimate bone age from a bone image, and the instructions include: estimating a RUS score for each of one or more partial bone images using a partial bone RUS score estimation model comprising one or more layers, and wherein the one or more partial bone images are generated from a whole bone image; and estimating bone age corresponding to the whole bone image using one or more RUS scores estimated for each of the one or more partial bone images, in which the partial bone RUS score estimation model is trained by using a labeled partial bone image as training data, and is trained by adjusting feature values calculated from the one or more layers.

20 Claims, 9 Drawing Sheets

(51) Int. Cl.
  *G16H 50/20* (2018.01)
  *G16H 50/30* (2018.01)
(52) U.S. Cl.
  CPC ............... *G06T 2207/20081* (2013.01); *G06T 2207/20084* (2013.01); *G06T 2207/20182* (2013.01); *G06T 2207/30008* (2013.01)
(58) Field of Classification Search
  CPC  G06T 2207/30008; G06T 2207/10116; G06N 3/047; G06N 3/045; G06N 3/084; G16H 50/20; G16H 50/30; G16H 30/40; A61B 6/032; A61B 5/004; A61B 5/1075; A61B 5/7246; A61B 6/505; A61B 6/5217; A61B 8/0875; A61B 5/055; A61B 5/7267; A61B 8/5223; A61B 2503/06; A61B 5/4504
  See application file for complete search history.

(56) References Cited

U.S. PATENT DOCUMENTS

| | | | | |
|---|---|---|---|---|
| 2003/0053673 | A1* | 3/2003 | Dewaele | G06T 7/0012 382/209 |
| 2017/0132512 | A1 | 5/2017 | Ioffe | |
| 2018/0116620 | A1* | 5/2018 | Chen | G06T 7/136 |
| 2018/0204111 | A1* | 7/2018 | Zadeh | G06V 10/764 |
| 2019/0206052 | A1* | 7/2019 | Hu | G06T 7/136 |
| 2019/0370662 | A1* | 12/2019 | Song | G06N 3/088 |
| 2019/0374185 | A1* | 12/2019 | Takahashi | A61B 6/463 |
| 2020/0020097 | A1* | 1/2020 | Do | G06F 18/2413 |
| 2020/0320685 | A1* | 10/2020 | Anssari Moin | G06T 7/11 |
| 2021/0110594 | A1* | 4/2021 | Teixeira | G06N 3/047 |
| 2021/0142477 | A1* | 5/2021 | Tsai | G06T 7/0012 |
| 2023/0128560 | A1* | 4/2023 | Han | H04W 72/0453 370/329 |
| 2023/0284986 | A1* | 9/2023 | Wang | G06T 11/008 |

OTHER PUBLICATIONS

Zhou, et al., "Objects as Point," Cornell University, 2019, https://arxiv.org/abs/1904.07850, 12 pages.

Zhang et al., "mixup: Beyond Empirical Risk Minimization," pp. 1-13, Apr. 27, 2018.

He et al., "Bag of Tricks for Image Classification with Convolutional Neural Networks," in 2019 *IEEE/CVF Conference on Computer Vision and Pattern Recognition (CVPR)*, Institute of Electrical and Electronics Engineers & The Computer Vision Foundation, Long Beach, CA, Jun. 15-20, 2019, pp. 558-567.

Oki et al., "Mixup of Feature Maps in a Hidden Layer for Training of Convolutional Neural Network," in *Proceedings Part II of the 25th International Conference on Neural Information Processing*, International Conference on Neural Information Processing, Siem Reap, Cambodia, Dec. 13-16, 2018, pp. 635-644.

* cited by examiner

BONE AGE ASSESSMENT METHOD FOR BONE IMAGE

CROSS-REFERENCE TO RELATED APPLICATIONS

This application claims priority to and the benefit of Korean Patent Application No. 10-2020-0076520 filed in the Korean Intellectual Property Office on Jun. 23, 2020, and Korean Patent Application No. 10-2020-0092344 filed in the Korean Intellectual Property Office on Jul. 24, 2020 the entire contents of which are incorporated herein by reference.

BACKGROUND

Technical Field

The present disclosure relates to a method of measuring bone age by using a machine learning module, and particularly, to a machine learning module which measures bone age from a bone image.

Description of the Related Art

In order to read bone age from a bone image in the related art, the Grulich-Pyle (GP) method and the Tanner-Whitehouse 3 (TW3) method were used.

The GP measurement method measures bone age by comparing and analyzing the hand bone photos of a target child by referring to the standard drawing of hand bone photos standardized by bone age at about 1 year interval. The GP measurement method enables a reader to quickly check the test result, but there is a problem that a focused area may be different depending on a reader and some deviations occur.

The TW3 measurement method determines the bone maturity grade for each of the 13 parts of the hand bone, and calculates the bone age by summing the scores corresponding to the grade. Unlike the GP measurement method, the TW3 measurement method generally evaluates the major growth plate areas in the hand bone, so that the deviation is little, but there is a problem in that it takes a long time to read and that the obscure 9-stage bone maturity classification level may affect the accuracy.

Accordingly, there may be a demand in the art for accurate bone age measurement technique in order to solve the problems.

BRIEF SUMMARY

The present disclosure is conceived in response to the background art, and has been made in an effort to provide a machine learning module which measures bone age from a bone image.

In order to solve the foregoing technical problems in the related art, there is disclosed a computer program stored in a computer readable storage medium. The computer program comprises instructions for causing one or more processors to estimate bone age from a bone image, and the instructions comprise: estimating a RUS score for each of one or more partial bone images using a partial bone RUS score estimation model comprising one or more layers, and wherein the one or more partial bone images are generated from a whole bone image; and estimating bone age corresponding to the whole bone image using one or more RUS scores estimated for each of the one or more partial bone images, in which the partial bone RUS score estimation model is trained by using a labeled partial bone image as training data, and is trained by adjusting feature values calculated from the one or more layers.

Alternatively, the partial bone RUS score estimation model may be trained by adjusting two or more feature values calculated from a hidden layer of the partial bone RUS score estimation model for each of two or more training data labeled with a RUS score through mix-up.

Alternatively, the mix-up may comprise an operation of exchanging at least a part of a first feature value corresponding to one training data calculated from the hidden layer of the partial bone RUS score estimation model with at least a part of a second feature value corresponding to other training data calculated from the hidden layer of the partial bone RUS score estimation model.

Alternatively, the partial bone RUS score estimation model may be trained based on a RUS score labeled on each of the two or more training data which is adjusted based on the mix-up.

Alternatively, the RUS score labeled on each of the two or more training data may comprise one or more classes, in which each of the one or more classes may have an ordered correlation based on ground truth.

Alternatively, the RUS score labeled on each of the two or more training data may be adjusted based on a weight related on a degree of the mix-up and a calculation result for each of the one or more classes.

Alternatively, the RUS score labeled on each of the two or more training data may be generated in a distribution form by performing label smoothing on a label of the RUS score.

Alternatively, a RUS score labeled on one training data may be adjusted based on a weight and a calculation result of a class of the RUS score, and wherein the weight is determined based on a degree of exchange between at least a part of a first feature value corresponding to one training data calculated from the hidden layer of the partial bone RUS score estimation model and at least a part of a second feature value corresponding to other training data calculated from the hidden layer of the partial bone RUS score estimation model.

Alternatively, the one or more partial bone images may be generated based on one or more major points and a size of a partial bone image corresponding to the one or more major points, and the one or more major points may be determined based on a probability that each of one or more points comprised in the whole bone image corresponds to a major point, and the size of a partial bone image may be determined based on a type of the one or more major points.

In order to solve the foregoing technical problems in the related art, there is disclosed a computing device estimating bone age from a bone image. The computing device may comprise: a memory comprising computer executable components; and a processor that executes the following computer executable components stored in the memory, in which the processor is configured to: estimate a RUS score for each of one or more partial bone images using a partial bone RUS score estimation model comprising one or more layers, in which the one or more partial bone images are generated from a whole bone image; and estimate bone age corresponding to the whole bone image using one or more RUS scores estimated for each of the one or more partial bone images, and the partial bone RUS score estimation model is trained by using a labeled partial bone image as training data, and is trained by adjusting feature values calculated from the one or more layers.

In order to solve the foregoing technical problems in the related art, there is disclosed a method of estimating bone age from a bone image by computing device. The method comprises: estimating a RUS score for each of one or more partial bone images using a partial bone RUS score estimation model comprising one or more layers, and wherein the one or more partial bone images are generated from a whole bone image; and estimating bone age corresponding to the whole bone image using one or more RUS scores estimated for each of the one or more partial bone images, in which the partial bone RUS score estimation model is trained by using a labeled partial bone image as training data, and is trained by adjusting feature values calculated from the one or more layers.

In order to solve the foregoing technical problems in the related art, there is disclosed a computer program stored in a computer readable medium in which a data structure storing parameters determining an operation of a model is stored. The parameter is determined based on a training method of the model, and the training method comprises: inputting two or more partial bone images on which RUS scores are labelled to a partial bone RUS score estimation model; adjusting at least a part of a feature value for one partial bone image among the two or more partial bone images calculated in a hidden layer of the partial bone RUS score estimation model based on at least a part of a feature value for another partial bone image calculated in the hidden layer of the partial bone RUS score estimation model; adjusting the RUS score labeled on each of the two or more partial bone images; and updating a parameter of the partial bone RUS score estimation model based on the adjusted RUS score and the RUS score output from the partial bone RUS score estimation model.

The present disclosure may provide a machine learning module for reading bone age from a bone image and a method of training the machine learning module.

DETAILED DESCRIPTION

Figure 1:
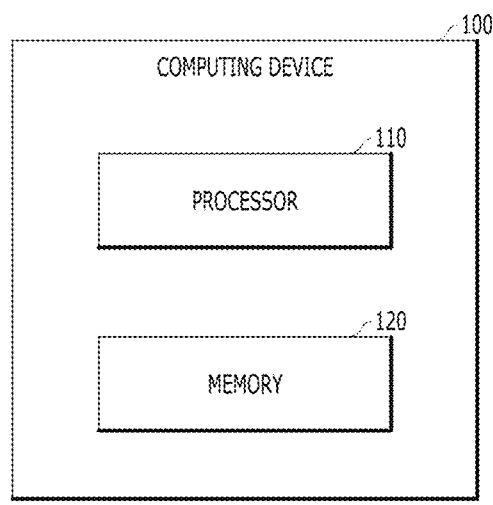
FIG. 1 is a block diagram illustrating a computing device for measuring bone age of a whole bone image by a processor according to an embodiment of the present disclosure.

Various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and a computing device may be components. One or more components may reside within a processor and/or an execution thread. One component may be localized within one computer. One component may be distributed between two or more computers. Further, the components may be executed by various computer readable media having various data structures stored therein. For example, components may communicate through local and/or remote processing according to a signal (for example, data transmitted to another system through a network, such as the Internet, through data and/or a signal from one component interacting with another component in a local system and a distributed system) having one or more data packets.

A term "or" intends to mean comprehensive "or" not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

It should be understood that a term "include" and/or "including" means that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear in context that a single form is indicated in context, the singular shall be construed to generally mean "one or more" in the present specification and the claims.

The term "at least one of A and B" should be interpreted to mean "the case including only A," "the case including only B," and "the case where A and B are combined."

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In the present disclosure, a network function, an artificial neural network, and a neural network may be interchangeably used.

The term "image" or "image data" used throughout the detailed description and the claims of the present disclosure refer to multidimensional data composed of discrete image elements (for example, pixels in a 2-dimensional image), and in other words, is the term referring to a target visible to the eye (displayed on a video screen) or a digital representation of the target (for example, a file corresponding to a pixel output of a CT or MRI detector).

For example, "image" or "picture" may be a medical image of a subject collected by Computed Tomography (CT), Magnetic Resonance Imaging (MRI), fundus image, ultrasonic rays, or other predetermined (or selected) medical imaging systems publicly known in the art of the present disclosure. The image is not necessarily provided in a medical context, but may also be provided in a non-medical context, such as X-ray imaging for security screening.

Throughout the detailed description and the claims of the present disclosure, the "Digital Imaging and Communications in Medicine (DICOM)" standard is a term collectively referring to various standards used in digital imaging expression and communication in medical devices, and the DICOM standard is published by the allied committee formed by the American College of Radiology (ACR) and American National Electrical Manufacturers Associations (NEMA).

Throughout the detailed description and the claims of the present disclosure, a "Picture Archiving and Communication System (PACS)" is a term that refers to a system that stores, processes, and transmits images in accordance with the DICom standard, and medical images obtained by using digital medical imaging equipment, such as X-ray, CT, and MRI, may be stored in the DICOM format and transmitted to terminals inside and outside a hospital through a network, and a reading result and a medical record may be added to the medical image.

FIG. 1 is a block diagram illustrating a computing device according to an embodiment of the present disclosure.

The configuration of a computing device 100 illustrated in FIG. 1 is merely a simplified example. In the embodiment of the present disclosure, the computing device 100 may include other configurations for performing a computing environment of the computing device 100, and only some of the disclosed configurations may also configure the computing device 100.

The computing device 100 may include a processor 110, a memory 120, and a network unit (not illustrated).

The processor 110 may be formed of one or more cores, and may include a processor, such as a central processing unit (CPU), a general purpose graphics processing unit (GPGPU), and a tensor processing unit (TPU) of the computing device, for performing a data analysis and deep learning. The processor 110 may read a computer program stored in the memory and perform data processing for machine learning according to the embodiment of the present disclosure. According to the embodiment of the present disclosure, the processor 110 may perform calculation for training a neural network. The processor 110 may perform a calculation, such as processing of input data for training in Deep Learning (DN), extraction of a feature from input data, an error calculation, and updating of a weight of the neural network by using backpropagation, for training the neural network. At least one of the CPU, GPGPU, and TPU of the processor 110 may process training of a network function. For example, the CPU and the GPGPU may process training of the network function and data classification by using a network function together. Further, in the embodiment of the present disclosure, the training of the network function and the data classification by using a network function may be processed by using the processors of the plurality of computing devices together. Further, the computer program executed in the computing device according to the embodiment of the present disclosure may be a CPU, GPGPU, or TPU executable program.

According to the embodiment of the present disclosure, the memory 120 may store a predetermined (or selected) type of information generated or determined by the processor 110 and a predetermined (or selected) type of information received by a network unit.

According to the embodiment of the present disclosure, the memory 120 may include at least one type of storage medium among a flash memory type, a hard disk type, a multimedia card micro type, a card type of memory (for example, an SD or XD memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk. The computing device 100 may also be operated in relation to web storage performing a storage function of the memory 120 on the Internet. The description of the foregoing memory is merely illustrative, and the present disclosure is not limited thereto.

The network unit according to the embodiment of the present disclosure may use various wired communication systems, such as a Public Switched Telephone Network (PSTN), an x Digital Subscriber Line (xDSL), a Rate Adaptive DSL (RADSL), a Multi Rate DSL (MDSL), a Very High Speed DSL (VDSL), a Universal Asymmetric DSL (UADSL), a High Bit Rate DSL (HDSL), and a local area network (LAN).

The network unit presented in the present specification may use various wireless communication systems, such as Code Division Multi Access (CDMA), Time Division Multi Access (TDMA), Frequency Division Multi Access (FDMA), Orthogonal Frequency Division Multi Access (OFDMA), Single Carrier-FDMA (SC-FDMA), and other systems.

The network unit in the present disclosure may be configured regardless of its communication mode, such as a wired mode and a wireless mode, and may be configured of various communication networks, such as a Personal Area Network (PAN) and a Wide Area Network (WAN). Further, the network may be the publicly known World Wide Web (WWW), and may also use a wireless transmission technology used in PAN, such as Infrared Data Association (IrDA) or Bluetooth.

The technologies described in the present specification may be used in other networks, as well as the foregoing networks.

Figure 2:
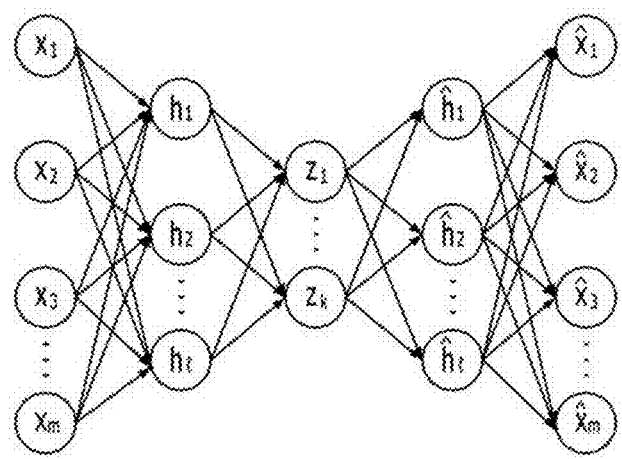
FIG. 2 is a schematic diagram illustrating a network function according to the embodiment of the present disclosure.

FIG. 2 is a schematic diagram illustrating a network function according to the embodiment of the present disclosure.

Throughout the present specification, a calculation model, a nerve network, the network function, and the neural network may be used with the same meaning. The neural network may be formed of a set of interconnected calculation units which are generally referred to as "nodes." The "nodes" may also be called "neurons." The neural network consists of one or more nodes. The nodes (or neurons) configuring the neural network may be interconnected by one or more links.

In the neural network, one or more nodes connected through the links may relatively form a relationship of an input node and an output node. The concept of the input node is relative to the concept of the output node, and a predetermined (or selected) node having an output node relationship with respect to one node may have an input node relationship in a relationship with another node, and a reverse relationship is also available.

As described above, the relationship between the input node and the output node may be generated based on the link. One or more output nodes may be connected to one input node through a link, and a reverse case may also be valid.

In the relationship between an input node and an output node connected through one link, a value of the output node data may be determined based on data input to the input node. Herein, a link connecting the input node and the output node may have a weight. The weight is variable, and in order for the neural network to perform a desired function, the weight may be varied by a user or an algorithm. For example, when one or more input nodes are connected to one output node by links, respectively, a value of the output node may be determined based on values input to the input nodes connected to the output node and weights set in the link corresponding to each of the input nodes.

As described above, in the neural network, one or more nodes are connected with each other through one or more links to form a relationship of an input node and an output node in the neural network. A characteristic of the neural network may be determined according to the number of nodes and links in the neural network, a correlation between the nodes and the links, and a value of the weight assigned to each of the links. For example, when there are two neural networks in which the numbers of nodes and links are the same and the parameter values between the links are different, the two neural networks may be recognized to be different from each other.

The neural network may consist of a set of one or more nodes. A subset of the nodes forming the neural network may form a layer. Some of the nodes configuring the neural network may form one layer based on distances from an initial input node. For example, a set of nodes having a distance of n from an initial input node may form n layers. The distance from the initial input node may be defined by the minimum number of links, which is beneficial to be passed from the initial input node to a corresponding node. However, the definition of the layer is arbitrary for the description, and a degree of the layer in the neural network may be defined by a different method from the foregoing method. For example, the layers of the nodes may be defined by a distance from a final output node.

The initial input node may mean one or more nodes to which data is directly input without passing through a link in a relationship with other nodes among the nodes in the neural network. Otherwise, the initial input node may mean nodes which do not have other input nodes connected through the links in a relationship between the nodes based on the link in the neural network. Similarly, the final output node may mean one or more nodes that do not have an output node in a relationship with other nodes among the nodes in the neural network. Further, the hidden node may mean nodes configuring the neural network, not the initial input node and the final output node.

In the neural network according to the embodiment of the present disclosure, the number of nodes of the input layer may be the same as the number of nodes of the output layer, and the neural network may be in the form that the number of nodes decreases and then increases again from the input layer to the hidden layer. Further, in the neural network according to another embodiment of the present disclosure, the number of nodes of the input layer may be smaller than the number of nodes of the output layer, and the neural network may be in the form that the number of nodes decreases from the input layer to the hidden layer. Further, in the neural network according to another embodiment of the present disclosure, the number of nodes of the input layer may be larger than the number of nodes of the output layer, and the neural network may be in the form that the number of nodes increases from the input layer to the hidden layer. The neural network according to another embodiment of the present disclosure may be the neural network in the form in which the foregoing neural networks are combined.

A deep neural network (DNN) may mean the neural network including a plurality of hidden layers, in addition to an input layer and an output layer. When the DNN is used, it is possible to recognize a latent structure of data. That is, it is possible to recognize the latent structures of pictures, texts, videos, voices, and music (for example, an object included in the picture, the contents and the emotion of the text, and the contents and the emotion of the voice). The DNN may include a convolutional neural network (CNN), a recurrent neural network (RNN), an auto encoder, Generative Adversarial Networks (GAN), a restricted Boltzmann machine (RBM), a deep belief network (DBN), a Q network, a U network, a Siamese network, and the like. The foregoing description of the deep neural network is merely illustrative, and the present disclosure is not limited thereto.

In the embodiment of the present disclosure, the network function may include an auto encoder. The auto encoder may be one type of artificial neural network for outputting output data similar to input data. The auto encoder may include at least one hidden layer, and the odd-numbered hidden layers may be disposed between the input/output layers. The number of nodes of each layer may decrease from the number of nodes of the input layer to an intermediate layer called a bottleneck layer (encoding), and then be expanded symmetrically with the decrease from the bottleneck layer to the output layer (symmetric with the input layer). The auto encoder may perform a nonlinear dimension reduction.

The number of input layers and the number of output layers may correspond to the dimensions after preprocessing of the input data. In the auto encoder structure, the number of nodes of the hidden layer included in the encoder decreases as a distance from the input layer increases. When the number of nodes of the bottleneck layer (the layer having the smallest number of nodes located between the encoder and the decoder) is too small, the sufficient amount of information may not be transmitted, so that the number of nodes of the bottleneck layer may be maintained in a specific number or more (for example, a half or more of the number of nodes of the input layer and the like).

The neural network may be trained by at least one scheme of supervised learning, unsupervised learning, semi-supervised learning, and reinforcement learning. The training of the neural network may be a process of applying knowledge for the neural network to perform a specific operation to the neural network.

The neural network may be trained in a direction of reducing or minimizing an error of an output. In the training of the neural network, training data is repeatedly input to the neural network and an error of an output of the neural network for the training data and a target is calculated, and the error of the neural network is back-propagated in a direction from an output layer to an input layer of the neural network in order to decrease the error, and a weight of each node of the neural network is updated. In the case of the supervised learning, training data labelled with a correct answer (that is, labelled training data) is used, in each training data, and in the case of the unsupervised learning, a correct answer may not be labelled to each training data. That is, for example, the training data in the supervised learning for data classification may be data, in which category is labelled to each of the training data. The labelled training data is input to the neural network and the output (category) of the neural network is compared with the label of the training data to calculate an error. For another example, in the case of the unsupervised learning related to the data classification, training data that is the input is compared with an output of the neural network, so that an error may be calculated. The calculated error is back-propagated in a reverse direction (that is, the direction from the output layer to the input layer) in the neural network, and a connection weight of each of the nodes of the layers of the neural network may be updated according to the backpropagation. A variation rate of the updated connection weight of each node may be determined according to a learning rate. The calculation of the neural network for the input data and the backpropagation of the error may configure a learning epoch. The learning rate is differently applicable according to the number of times of repetition of the learning epoch of the neural network. For example, at the initial stage of the learning of the neural network, a high learning rate is used to make the neural network rapidly secure performance of a predetermined (or selected) level and improve efficiency, and at the latter stage of the learning, a low learning rate is used to improve accuracy.

In the learning of the neural network, the training data may be generally a subset of actual data (that is, data to be processed by using the learned neural network), and thus an error for the training data is decreased, but there may exist a learning epoch, in which an error for the actual data is increased. Overfitting is a phenomenon, in which the neural network excessively learns training data, so that an error for actual data is increased. For example, a phenomenon, in which the neural network learning a cat while seeing a yellow cat cannot recognize cats, other than a yellow cat, as cats, is a sort of overfitting. Overfitting may act as a reason of increasing an error of a machine learning algorithm. In order to prevent overfitting, various optimizing methods may be used. In order to prevent overfitting, a method of increasing training data, a regularization method, a dropout method of inactivating a part of nodes of the network during the learning process, a method using a bath normalization layer, and the like may be applied.

According to the embodiment of the present disclosure, a computer readable medium storing a data structure is disclosed.

The data structure may refer to organization, management, and storage of data that enable efficient access and modification of data. The data structure may refer to organization of data for solving a specific problem (for example, data search, data storage, and data modification in the shortest time). The data structure may also be defined with a physical or logical relationship between the data elements designed to support a specific data processing function. A logical relationship between data elements may include a connection relationship between user defined data elements. A physical relationship between data elements may include an actual relationship between the data elements physically stored in a computer readable storage medium (for example, a permanent storage device). In particular, the data structure may include a set of data, a relationship between data, and a function or a command applicable to data. Through the effectively designed data structure, the computing device may perform a calculation while minimally using resources of the computing device. In particular, the computing device may improve efficiency of calculation, reading, insertion, deletion, comparison, exchange, and search through the effectively designed data structure.

The data structure may be divided into a linear data structure and a non-linear data structure according to the form of the data structure. The linear data structure may be the structure in which only one data is connected after one data. The linear data structure may include a list, a stack, a queue, and a deque. The list may mean a series of dataset in which order exists internally. The list may include a linked list. The linked list may have a data structure in which each data has a pointer and is linked in a single line. In the linked list, the pointer may include information about the connection with the next or previous data. The linked list may be expressed as a single linked list, a double linked list, and a circular linked list according to the form. The stack may have a data listing structure with limited access to data. The stack may have a linear data structure that may process (for example, insert or delete) data only at one end of the data structure. The data stored in the stack may have a data structure (Last In First Out, LIFO) in which the later the data enters, the sooner the data comes out. The queue is a data listing structure with limited access to data, and may have a data structure (First In First Out, FIFO) in which the later the data is stored, the later the data comes out, unlike the stack. The deque may have a data structure that may process data at both ends of the data structure.

The non-linear data structure may be the structure in which the plurality of pieces of data is connected after one data. The non-linear data structure may include a graph data structure. The graph data structure may be defined with a vertex and an edge, and the edge may include a line connecting two different vertexes. The graph data structure may include a tree data structure. The tree data structure may be the data structure in which a path connecting two different vertexes among the plurality of vertexes included in the tree is one. That is, the tree data structure may be the data structure in which a loop is not formed in the graph data structure.

Throughout the present specification, a calculation model, a nerve network, the network function, and the neural network may be used with the same meaning.

Hereinafter, the terms of the calculation model, the nerve network, the network function, and the neural network are unified and described with a neural network. The data structure may include a neural network. Further, the data structure including the neural network may be stored in a computer readable medium. The data structure including the neural network may also include preprocessed data for processing by the neural network, data input to the neural network, a weight of the neural network, a hyper-parameter of the neural network, data obtained from the neural network, an active function associated with each node or layer of the neural network, and a loss function for training of the neural network. The data structure including the neural network may include predetermined (or selected) configuration elements among the disclosed configurations. That is, the data structure including the neural network may include the entirety or a predetermined (or selected) combination of pre-processed data for processing by neural network, data input to the neural network, a weight of the neural network, a hyper parameter of the neural network, data obtained from the neural network, an active function associated with each node or layer of the neural network, and a loss function for training the neural network. In addition to the foregoing configurations, the data structure including the neural network may include predetermined (or selected) other information determining a characteristic of the neural network. Further, the data structure may include all types of data used or generated in a calculation process of the neural network, and is not limited to the foregoing matter. The computer readable medium may include a computer readable recording medium and/or a computer readable transmission medium. The neural network may be formed of a set of interconnected calculation units which are generally referred to as "nodes." The "nodes" may also be called "neurons." The neural network consists of one or more nodes.

The data structure may include data input to the neural network. The data structure including the data input to the neural network may be stored in the computer readable medium. The data input to the neural network may include training data input in the training process of the neural network and/or input data input to the training completed neural network. The data input to the neural network may include data that has undergone pre-processing and/or data to be pre-processed. The pre-processing may include a data processing process for inputting data to the neural network. Accordingly, the data structure may include data to be pre-processed and data generated by the pre-processing. The foregoing data structure is merely an example, and the present disclosure is not limited thereto.

The data structure may include a weight of the neural network. (in the present specification, weights and parameters may be used with the same meaning.) Further, the data structure including the weight of the neural network may be stored in the computer readable medium. The neural network may include a plurality of weights. The weight is variable, and in order for the neural network to perform a desired function, the weight may be varied by a user or an algorithm. For example, when one or more input nodes are connected to one output node by links, respectively, the output node may determine a data value output from the output node based on values input to the input nodes connected to the output node and the weight set in the link corresponding to each of the input nodes. The foregoing data structure is merely an example, and the present disclosure is not limited thereto.

For a non-limited example, the weight may include a weight varied in the neural network training process and/or the weight when the training of the neural network is completed. The weight varied in the neural network training process may include a weight at a time at which a training cycle starts and/or a weight varied during a training cycle. The weight of the training completed neural network may include a weight of the neural network completing the training cycle. Accordingly, the data structure including the weight of the neural network may include the data structure including the weight varied in the neural network training process and/or the weight of the training completed neural network. Accordingly, it is assumed that the weight and/or a combination of the respective weights are included in the data structure including the weight of the neural network. The foregoing data structure is merely an example, and the present disclosure is not limited thereto.

The data structure including the weight of the neural network may be stored in the computer readable storage medium (for example, a memory and a hard disk) after undergoing a serialization process. The serialization may be the process of storing the data structure in the same or different computing devices and converting the data structure into a form that may be reconstructed and used later. The computing device may serialize the data structure and transceive the data through a network. The serialized data structure including the weight of the neural network may be reconstructed in the same or different computing devices through deserialization. The data structure including the weight of the neural network is not limited to the serialization. Further, the data structure including the weight of the neural network may include a data structure (for example, in the non-linear data structure, B-Tree, Trie, m-way search tree, AVL tree, and Red-Black Tree) for improving efficiency of the calculation while minimally using the resources of the computing device. The foregoing matter is merely an example, and the present disclosure is not limited thereto.

The data structure may include a hyper-parameter of the neural network. The data structure including the hyper-parameter of the neural network may be stored in the computer readable medium. The hyper-parameter may be a variable varied by a user. The hyper-parameter may include, for example, a learning rate, a cost function, the number of times of repetition of the training cycle, weight initialization (for example, setting of a range of a weight value to be weight-initialized), and the number of hidden units (for example, the number of hidden layers and the number of nodes of the hidden layer). The foregoing data structure is merely an example, and the present disclosure is not limited thereto.

Figure 3:
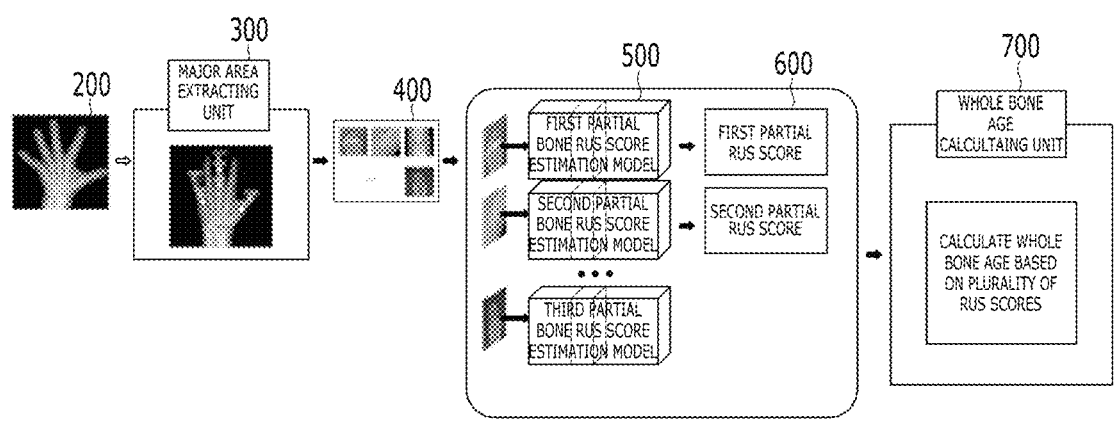
FIG. 3 is a diagram illustrating a process of measuring bone age in a whole bone image by the computing device according to the embodiment of the present disclosure.

FIG. 3 is a diagram illustrating a process of measuring bone age in a whole bone image by the computing device according to the embodiment of the present disclosure.

The processor 110 according to the present disclosure may estimate bone age from a bone image by executing a computer program stored in a computer-readable storage medium. To this end, the processor 110 may generate one or more partial bone image 400 from a whole bone image, estimate a partial RUS score for each of the one or more partial bone images 400, and measure a whole bone age of the whole bone image 200 by using one or more estimated partial RUS scores estimated for each of the one or more partial bone images 400. In this case, the partial RUS score 600 may be estimated by a partial bone RUS score estimation model 500. The partial bone RUS score estimation model 500 may be a machine learning module. When the partial bone RUS score estimation model 500 is built by using the machine learning module, a labelled partial bone image may be used as training data in training of the partial bone RUS score estimation model 500, and the training of the partial bone RUS score estimation model 500 may be performed through an adjustment of a feature value calculated in one or more layers.

Throughout the present disclosure, the adjustment for the feature value may mean the performance of mix-up on the feature values for each of two or more training data in the process of training the partial bone RUS score estimation model 500. The partial bone RUS score estimation model 500 may be trained based on a RUS score labeled on each of two or more training data adjusted based on the mix-up. The mix-up calculation will be described in detail below in relation to Equation 1 below.

In the present disclosure, the whole bone image 200 may be a bone image of a body part of which bone age needs to be measured. For example, the whole bone image 200 may include a marrow bone image, an elbow image, and other joint images, and may include an X-ray image capable of checking a shape of a bone, but the whole bone image 200 is not limited thereto.

The whole bone image 200 may include one or more major points. The one or more major points may be the points at which the RUS score 600 for measuring the bone age for the whole bone image 200 needs to be measured. That is, the processor 110 may estimate the RUS score 600 for each of the one or more major points, and measure the whole bone age by using the one or more estimated RUS scores 600.

In order to measure the RUS score 600 for each of the one or more major points, the whole bone image 200 may be divided into one or more partial bone images 400. To this end, a major area extracting unit 300 may not only extract one or more major points from the whole bone image 200, but also generate the partial bone image 400 including the extracted major points.

The processor 110 according to the present disclosure may generate the partial bone image 400 from the whole bone image 200 by using the major area extracting unit 300. The processor 110 may extract one or more major points included in the whole bone image 200 by using the major area extracting unit 300, and generate one or more partial bone images 400 by using the one or more extracted major points. The major area extracting unit 300 may be established as a machine learning module trained for extracting one or more major points from the whole bone image 200. The major area extracting unit 300 may be trained so as to reduce or minimize a loss function that compares whether one or more pixels included in the whole bone image 200 correspond to one or more major points included in the whole bone image 200 with ground truth related to the major point. In particular, the major area extracting unit 300 may calculate a probability that the corresponding pixel corresponds to the major point for each of the one or more pixels included in the whole bone image 200. When the probability that the predetermined (or selected) pixel corresponds to the major point is larger than a predetermined (or selected) reference value, the major area extracting unit 300 may determine the predetermined (or selected) pixel as the major point. Further, the major area extracting unit 300 may classify the major point by type. That is, the major area extracting unit 300 may separately calculate a probability that a specific pixel corresponds to a first major point and a probability that a specific pixel corresponds to a second major point. In relation to this, the major area extracting unit 300 may generate a separate probability map for each type of major point.

The major area extracting unit 300 may generate one or more partial bone images 400 by using the extracted major point. For example, the major area extracting unit 300 may determine a size of the partial bone image 400 for each type of major point. The major area extracting unit 300 may determine a size of the partial bone image 400 by comparing the ground truth of the partial bone image area for each major point with the area of the partial bone image 400 generated by the major area extracting unit 300. In particular, the major area extracting unit 300 may be trained so that the loss function determined by using a difference in a discrepancy area between the partial bone image area for each major point and the partial bone image 400 generated by the major area extracting unit 300 is reduced or minimized. The size of the partial bone image 400 may be differently determined according to the type of major point. However, in order to reduce the amount of calculation required for the training of the major area extracting unit 300 in relation to the determination of the size of the partial bone image 400, the size of the partial bone image 400 may also be collectively determined regardless of the type of major area.

In the present disclosure, the partial bone image 400 may be the divided part of the whole bone image 200. The partial bone image 400 may include one or more major points for measuring bone age therein. As described above, the partial bone image 400 may be generated based on the extracted major point and the size of the partial bone image 400 according to the type of extracted major point. In this case, the major point may be located at the center of the partial bone image 400.

In the present disclosure, the partial bone RUS score estimation model 500 may be a computer-executable component which receives the partial bone image 400 and generates the RUS score 600 corresponding to the input partial bone image 400. The partial bone RUS score estimation model 500 according to the present disclosure may be configured as a machine leaning module for generating the RUS score. The partial bone RUS score estimation model 500 may be formed of one or more artificial neural networks, and the number of artificial neural networks may be based on the number of partial bone images 40 for the input data. That is, the partial bone RUS score estimation model 500 may include a sub module for classifying the partial bone image.

The partial bone RUS score estimation model 500 according to the present disclosure may be trained to receive the partial bone image 400 as an input and estimate the RUS score 600 for the input partial bone image 400. In order to train the partial bone RUS score estimation model 500, supervised learning, unsupervised learning, and semi supervised learning, and the like may be used. The training data for training the partial bone RUS score estimation model 500 may include the partial bone image 400 and a label for the RUS score of the partial bone image.

In the present disclosure, the training data for the partial bone RUS score estimation model 500 may be adjusted. The adjustment of the training data may include the adjustment of a feature value and a RUS score label value for the partial bone image 400. That is, the mix-up calculation for the training data may be performed on both the feature value and the RUS score label value.

In particular, the adjustment of the training data is to generate a new feature value by combining feature values of the same type by predetermined (or selected) logic in the partial bone image 400 for two or more training data. Further, the adjustment of the RUS score label value may include generation of a new label value by combining bone age initial labels for the partial bone images 400 for two or more training data by a predetermined (or selected) logic. The combination of the bone age initial label may include performance of the mix-up calculation for one or more bone age initial labels. Further, the adjustment of the RUS score label may include performance of label smoothing by using the generated new label value.

For example, in order to train the partial bone RUS score estimation model 500 according to the present disclosure, the partial bone image 400 that is the input data may be adjusted. The mix-up calculation may include an operation of mixing feature values calculated from a hidden layer of the partial bone RUS score estimation model of each of the training data included in a group, in the group including two or more training data. The mix-up calculation may include an operation of exchanging at least a part of the feature value of one training data calculated from the hidden layer of the partial bone RUS score estimation model among two or more training data with at least a part of the feature value of another training data calculated from the hidden layer of the partial bone RUS score estimation model. For example, it is assumed that there are a first feature value of a partial bone image of first training data calculated from the hidden layer of the partial bone RUS score estimation model and a second feature value of a partial bone image of second training data calculated from the hidden layer of the partial bone RUS score estimation model. In this case, the partial bone image of the first training data and the partial bone image of the second training data may have different RUS score classes and may be the partial bone images for the same anatomical location. The first feature value and the second feature value may be formed in the form of vector having the same dimension. At least a part of the first feature value and at least part of the second feature value may be exchanged with each other and be mixed up, and at least a part of each vector to be mixed up may be the part related to a corresponding feature. Further, for example, the feature values of each of the training data included in the training data subset including two or more training data may be exchanged with each other and mixed up. In this case, the RUS scores labeled on the training data included in the training data subset, respectively, so that the feature values are exchanged with each other and mixed up may have a predetermined (or selected) distribution. In this case, the RUS score labelled to each of the mixed-up training data may be a class in a predetermined (or selected) range. For example, first training data labeled with a RUS score that may be converted to bone age 10 and second training data labeled with a RUS score that may be converted to bone age 1 may not constitute the training data subset, and third training data labeled with a RUS score that may be converted to bone age 5 and fourth training data labeled with a RUS score that may be converted to bone age 6 may constitute the training data subset for the mix-up. That is, the RUS score labeled on each training data in the present disclosure may have one or more classes, and each class may have an ordered correlation based on actual information (for example, bone age). In this case, mix-up of training data labeled with RUS scores that are too far out of class may be undesirable. Accordingly, in order for the training data corresponding to the labels in which the distance between the classes (that is, the distance of the actual information (for example, bone age) of the class) is within a predetermined (or selected) range to be mixed up, the processor 110 may determine the training data subset for performing the mix-up.

The partial bone image 400 that is the input data may be adjusted by combining the feature values at the same point in the partial bone images 400 for two or more training data for the same major point by a predetermined (or selected) logic. The predetermined (or selected) logic for the combination of the pixel feature values may include performance of the mix-up calculation on the pixel feature value. For example, it is assumed that there are the partial bone images 400 for two or more training data for the first major point. Herein, the adjustment of the partial bone image 400 may be adding the feature values of the pixels at the same point in two or more partial bone images 400 by a predetermined (or selected) logic. Herein, the predetermined (or selected) logic for adjusting the partial bone image may be the mix-up calculation, and the particular calculation method of the mix-up calculation may be expressed by Equation 1 below.

$$M_\lambda(a,b)=\lambda a+(1-\lambda)b \qquad \text{Equation 1}$$

In Equation 1, $M_\lambda(a,b)$ may be the adjusted feature value in a specific pixel.

a and b may be feature values of the specific pixel in the two partial bone images 400 for the first major point. $\lambda$ may be a predetermined (or selected) hyper parameter determined for generating the adjusted feature value, and for example, may be a random variable (for example, beta-distribution) according to a specific distribution.

In order to train the partial bone RUS score estimation model 500, the processor 110 may make the adjustment of the feature value of the partial bone image 400 be performed in the hidden layer in the training operation of the partial bone RUS score estimation model 500. That is, the mix-up calculation according to the present disclosure may also be performed on the feature values in the hidden layer. The adjustment of the feature value of the partial bone image 400 in the hidden layer may be a determination of the one or more calculated initial feature values and the adjusted feature value generated based on the Opredetermined (or selected) logic as an input feature value of a next layer in order to perform normalization of hidden representations of the partial bone image. The predetermined (or selected) logic applied to the initial feature value may be the mix-up calculation. In particular, the adjustment of the initial feature value of the partial bone image 400 may be performed by combining the initial feature values of the same type (for example, a start node and an arrival node of the transmitted feature value are the same) in the two or more partial bone images 400 for the same major point by the predetermined (or selected) logic. For example, it is assumed that there are two or more partial bone images 400 for the first major point. Herein, the adjustment of the initial feature values of the partial bone images 400 in the hidden layer may be the addition of the initial feature values of the same type by the predetermined (or selected) logic. Herein, the predetermined (or selected) logic for adjusting the initial feature value in the hidden layer may be represented by Equation 1 below. Herein, the hyper parameter is the value determined for performing the adjustment for the hidden layer, and may be different from a value determined for performing the adjustment for the input layer. The partial bone RUS score estimation model 500 may input the feature value adjusted by the predetermined (or selected) logic to a next layer.

In the present disclosure, the label of the training data for the partial bone RUS score estimation model 500 may be adjusted. The adjustment of the label may be performed by using the initial label of the partial bone image 400 for each of the two or more training data for one major point. In particular, the processor 110 may generate initial labels for the partial bone images 400 for one major point and an adjusted label value by using Equation 1.

In more particular, the RUS score labeled on each of the training data may include one or more classes, and each of the classes may have an ordered correlation based on ground truth (for example, bone age). That is, the RUS score may correspond to bone age, and the class of the RUS score may represent bone age, and one or more classes of the RUS score may have an ordered correlation.

The RUS score labeled on each of the training data may be adjusted based on the weight based on the degree of mix-up performed on the training data subset including two or more training data and the calculation result for each class. The RUS score labeled on the training data may be adjusted based on the weight determined based on the degree of the exchange between at least a part of the feature value (the first feature value) for the first training data calculated in the hidden layer of the partial bone RUS score estimation model and at least a part of the feature value (the second feature value) for the second training data calculated in the hidden layer of the partial bone RUS score estimation model and the calculation result for the class of the RUS score.

For example, it is assumed there is a training data subset including the first training data and the second training data. It is assumed that the RUS score representing bone age 4 is labeled on the first training data and the RUS score representing bone age 6 is labeled on the second training data. In this case, in the process of training the partial bone RUS score estimation model, when the feature value of the first training data and the feature value of the second training data are mixed at a ratio of 50% (for example, 50% of the components of the feature value of the first training data is converted to 50% of the components of the feature value of the second training data), the RUS score representing the bone age 4 labeled on the first training data may be adjusted to the RUS score representing bone age 5. That is, in the case where the feature value of other training data is mixed with the feature value of one training data, the RUS score labeled on one training data may be adjusted to be close to the RUS score labeled on other training data as more feature values of other training data are mixed up based on the degree of the mix-up of the feature value of other training data.

The processor 110 may generate a label distribution for the RUS score. In the present disclosure, the label distribution may be the distribution such that the RUS scores are continuous rather than discrete. In the present disclosure, the label distribution includes numerical values corresponding to two or more labels for the RUS score. For example, the label distribution may include a plurality of labels for the RUS Score 600 of the partial bone image 400 and a numerical value corresponding to each of the corresponding labels. For example, it is assumed that an initial label for a RUS score of a predetermined (or selected) partial bone image 400 is the RUS score corresponding to bone age 6. In this case, the bone age initial label may be the form of one-hot encoding. In contrast, the label distribution of the RUS score for the predetermined (or selected) partial bone age 400 may have the form of (age 4, age 5, age 6, age 7, age 8)=(0.1, 0.2, 0.4, 0.2, 0.2). The label distribution may be the expression about the degree to which each of the RUS score labels describes the partial bone image 400. In the label distribution, the sum of the numerical values corresponding to the labels may be 1. In this case, the numerical value corresponding to the label distribution may also be understood as a probability that the RUS score of the predetermined (or selected) partial bone image 400 corresponds to a specific label. The processor 110 may generate the label distribution for the bone age by performing label smoothing from the initial label of the bone age or the adjusted label of the bone age. The label smoothing may be performed by applying the kernel function on the initial label of the bone age or the adjusted label of the bone age. Herein, the kernel function for performing the label smoothing may be Gaussian kernel.

The adjustment and the label smoothing of the input data, the initial feature value in the hidden layer, and the bone age initial label may be applied to the training data of the partial bone RUS score estimation model 500 at the same time. That is, the partial bone RUS score estimation model 500 may be trained by using the label distribution generated by performing the label smoothing on the adjusted input data, the adjusted one or more feature values in the hidden layer, and the adjusted label value generated based on the initial label.

The bone age indicates the degree of growth of a person, and is not a discrete value, but when the training is performed by using the discrete label, there is a disadvantage in that it is difficult to provide continuous inference results. In the embodiment of the present disclosure, it is possible to provide continuous inference results by mixing up the subsets of the training data and adjusting the RUS score labeled on each training data to have a more continuous value based on the mix-up (that is, so as to decrease an interval between the classes of the RUS score). That is, in the embodiment of the present disclosure, when bone age of a bone age measurement target is inferred, it may be easier to infer more accurate values that are closer to real age, such as age 4.1 and age 4.8, rather than rather discrete values, such as age 4, age 5, and age 6.

The machine learning modules including deep learning in the related art present the accurate inference result when a distance between classes is large, but have a disadvantage in that the machine learning modules cannot present the accurate inference result when the distance between the classes is small (that is, when the class is subdivided). By mixing at least one of the feature value and the label of the training data according to the present disclosure, various types of training data presenting in the middle of the class may be generated. Further, it is possible to prevent overfitting of the partial bone RUS score estimation model 500 by adjusting not only the input data and the output data, but also the hidden representation expressed by the feature value generated in the hidden layer.

In the present disclosure, the partial bone RUS score estimation model 500 may receive the partial bone image 400 as an input and generate the RUS score 600 of the partial bone image 400. As illustrated in FIG. 3, the partial bone RUS score estimation model 500 may exist for each of the partial bone images 400. Accordingly, the RUS score 600 may also be present for each of the one or more partial bone images 400.

The RUS score 600 is output data of the partial bone RUS score estimation model 500, so that the RUS score 600 may be generated in the one-hot encoding form of the label or the label distribution form like the training data of the partial bone RUS score estimation model 500. That is, the trained partial bone RUS score estimation model 500 may generate the RUS score 600 in the label distribution form for the partial bone image 400. In this case, the processor 110 may also determine the label in which the numerical value corresponding to the label value is highest in the label distribution generated by the partial bone RUS score estimation model 500 as the RUS score 600.

A whole bone age calculation unit 700 according to the present disclosure may generate whole bone age by combining the one or more RUS scores 600 generated by the one or more partial bone RUS score estimation models 500. The whole bone age calculation unit 700 may measure a whole bone age for the whole bone image 200 based on a predetermined (or selected) RUS score—bone age conversion table. In this case, the RUS score—bone age conversion table may be different depending on a gender of the whole bone image 200.

Figure 4:
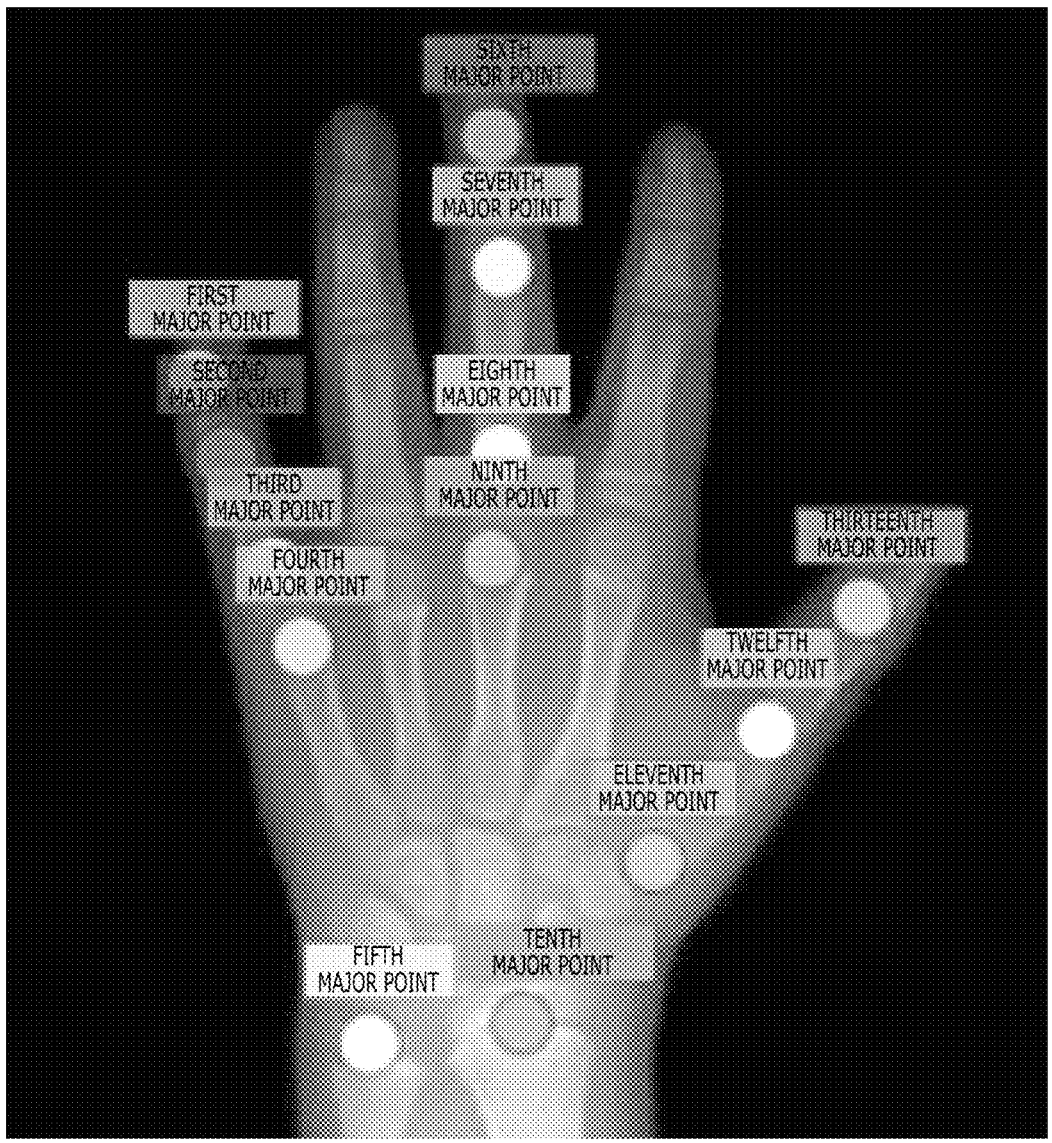
FIG. 4 is a diagram illustrating one or more main points for the whole bone image according to the embodiment of the present disclosure.

FIG. 4 is a diagram illustrating one or more main points for the whole bone image according to the embodiment of the present disclosure.

In the present disclosure, the major point may be the point at which the RUS score is measured. One or more of the major points may be included in the whole bone image 200. Referring to FIG. 4, the whole bone image 200 illustrated in FIG. 4 may include one or more major points. That is, the whole bone image 200 may include the first major point to a thirteenth major point. The first major point to the thirteenth major point may be the points for measuring the RUS score that is the basis of the generation of the whole bone age for the whole bone image. The processor 110 according to the present disclosure may extract the first major point to the thirteenth major point form the whole bone image 200 by using the major area extracting unit 300. The processor 110 may generate one or more partial bone images 400 including the major point by using the extracted major point.

Hereinafter, the method of generating the partial bone image 400 will be described in detail.

The processor 110 according to the present disclosure may generate the partial bone image 400 from the whole bone image 200 by using the major area extracting unit 300. The processor 110 may extract one or more major points included in the whole bone image 200 by using the major area extracting unit 300, and generate one or more partial bone images 400 by using the one or more extracted major points. The major area extracting unit 300 may be established as a machine learning module trained for extracting one or more major points from the whole bone image 200. The major area extracting unit 300 may be trained so as to reduce or minimize a loss function that compares whether one or more pixels included in the whole bone image 200 correspond to one or more major points included in the whole bone image 200 with ground truth related to the major point. In particular, the major area extracting unit 300 may calculate a probability that the corresponding pixel corresponds to the major point for each of the one or more pixels included in the whole bone image 200. When the probability that the predetermined (or selected) pixel corresponds to the major point is larger than a predetermined (or selected) reference value, the major area extracting unit 300 may determine the predetermined (or selected) pixel as the major point. Further, the major area extracting unit 300 may classify the major point by type. That is, the major area extracting unit 300 may separately calculate a probability that a specific pixel corresponds to a first major point and a probability that a specific pixel corresponds to a second major point. In relation to this, the major area extracting unit 300 may generate a separate feature map for each type of major point.

The major area extracting unit 300 may generate one or more partial bone images 400 by using the extracted major point. For example, the major area extracting unit 300 may determine a size of the partial bone image 400 for each type of major point. The major area extracting unit 300 may determine a size of the partial bone image 400 by comparing the ground truth of the partial bone image area for each major point with the area of the partial bone image 400 generated by the major area extracting unit 300. In particular, the major area extracting unit 300 may be trained so as to reduce or minimize the determined loss function by using a width of a discrepancy area between the partial bone image area for each of the major points and the partial bone image 400 generated by the major area extracting unit 300. The size of the partial bone image 400 may be differently determined according to the type of major point. However, in order to reduce the amount of calculation required for the training of the major area extracting unit 300 in relation to the determination of the size of the partial bone image 400, the size of the partial bone image 400 may also be collectively determined regardless of the type of major area.

Figure 5:
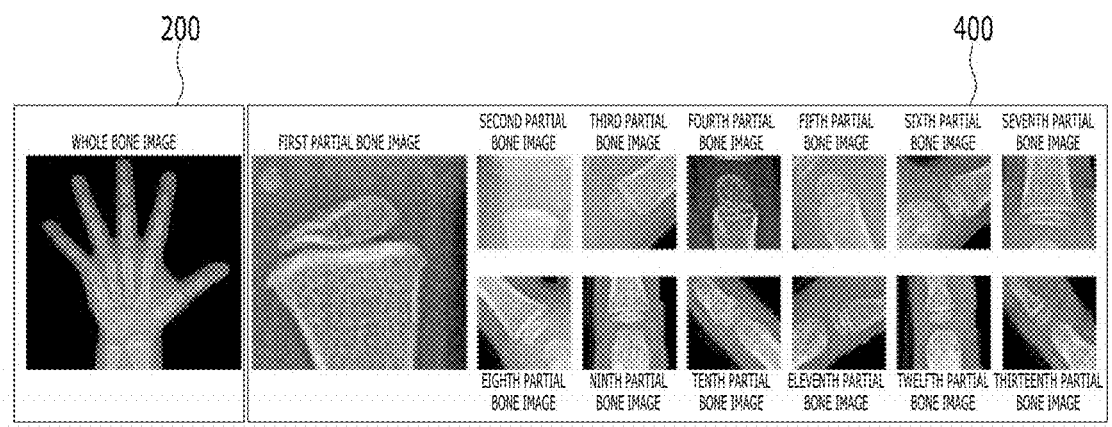
FIG. 5 is a diagram illustrating a whole bone image and a partial bone image according to the embodiment of the present disclosure.

FIG. 5 is a diagram illustrating a whole bone image and a partial bone image according to the embodiment of the present disclosure.

In the present disclosure, the whole bone image 200 may be the image of a body part in which bone age needs to be measured. The whole bone image 200 may include one or more major points. The one or more major points may be the points at which the RUS score 600 for measuring the bone age for the whole bone image 200 needs to be measured. That is, the processor 110 may estimate the RUS score 600 for each of the one or more major points, and calculate the whole bone age by using the one or more estimated RUS scores 600 information.

In order to measure the RUS score 600 for each of the one or more major points, the whole bone image 200 may be divided into one or more partial bone images 400. To this end, a major area extracting unit 300 may not only extract one or more major points from the whole bone image 200, but also generate the partial bone image 400 including the extracted major points.

In the present disclosure, the partial bone image 400 may be the divided part of the whole bone image 200. The partial bone image 400 may include one or more major points for measuring bone age therein. As described above, the partial bone image 400 may be generated based on the extracted major point and the size of the partial bone image 400 according to the type of extracted major point. In this case, the major point may be located at the center of the partial bone image 400.

As illustrated in FIG. 5, the plurality of partial bone images 400 may be generated for one whole bone image 200. The partial bone images 400 may correspond to the major points included in the whole bone image 200, respectively, and the corresponding major point may be included in the partial bone image 400.

Figure 6:
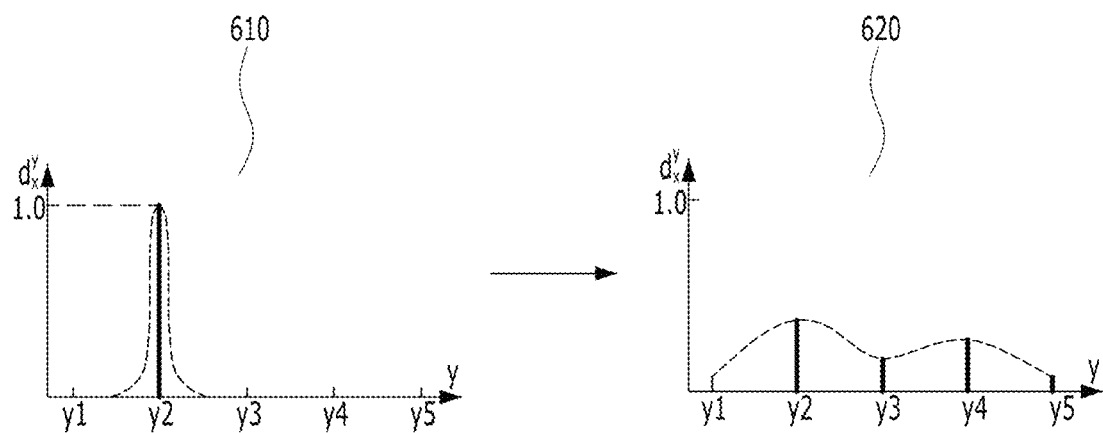
FIG. 6 is a diagram illustrating a bone age label distribution according to the embodiment of the present disclosure.

FIG. 6 is a diagram illustrating a bone age label distribution according to the embodiment of the present disclosure.

In the present disclosure, the label data of the training data for the partial bone RUS score estimation model 500 may be adjusted. In particular, the adjustment of the label of the training data may be performed through the mix-up calculation. The adjustment of the label data may be performed by using the initial labels of the two or more partial bone images 400 for one major point. In particular, the processor 110 may generate the initial labels of the two or more partial bone images 400 for one major point, and the adjusted label value by using Equation 1. In this case, the hyper parameter$^4$ for performing the adjustment on the initial label may be different from a hyper parameter for adjusting the input data or adjusting a specific value in the hidden layer.

The processor 110 may generate a label distribution for the RUS score value. In the present disclosure, the label distribution may include numerical values corresponding to two or more labels for the bone age for the bone image. For example, the label distribution may include a plurality of labels for the RUS Score 600 of the partial bone image 400 and a numerical value corresponding to each of the corresponding labels. For example, it is assumed that an initial label for a RUS score of a predetermined (or selected) partial bone image 400 is the RUS score corresponding to age 6. In this case, the bone age initial label may be the form of one-hot encoding. In contrast, the label distribution of the RUS score for the predetermined (or selected) partial bone age 400 may be (age 4, age 5, age 6, age 7, age 8)=(0.1, 0.2, 0.4, 0.2, 0.1) that is the probability form to correspond to the RUS scores corresponding to the bone ages. The label distribution may be the expression about the degree to which each of the RUS score labels describes the partial bone image 400. In the label distribution, the sum of the numerical values corresponding to the labels may be 1. In this case, the numerical value corresponding to the label distribution may also be understood as a probability that the bone age of the predetermined (or selected) partial bone image 400 corresponds to a specific label. The processor 110 may generate the label distribution for the RUS score by performing label smoothing from the initial label of the RUS score or the adjusted label of the RUS score. The label smoothing may be performed by applying the Kernel function on the initial label of the RUS score or the adjusted label of the RUS score. Herein, the kernel function for performing the label smoothing may be Gaussian kernel.

The adjustment and the label smoothing for the input data, the feature value in the hidden layer, and the initial label of the RUS score may be applied to the training data of the partial bone RUS score estimation model 500. That is, the partial bone RUS score estimation model 500 may be trained by using the label distribution generated by performing the label smoothing on the adjusted input data, the adjusted one or more feature values in the hidden layer, and the adjusted label value generated based on the initial label.

This will be described with reference to FIG. 6. In the present disclosure, the initial label of the RUS score may be expressed like an initial label graph 610. That is, the initial label of the RUS score may be expressed as 1 for a specific class ($y_2$) for one partial bone image and as 0 for the remaining classes. The initial label of the RUS score may be expressed like the initial label graph 610 or may be implemented in the form of one-hot encoding. However, the RUS score label distribution according to the present disclosure may be expressed like a label distribution graph 620. In this case, each of the numerical value for the RUS score label may indicate the degree to which each RUS score label is explained for the partial bone image 400 or may be a probability that the RUS score of the partial bone image 400 is the corresponding label. In particular, the RUS score label distribution may be expressed like (age 4, age 5, age 6, age 7, age 8)=(0.1, 0.2, 0.4, 0.2, 0.1) that is the probability form to correspond to the RUS scores corresponding to the bone ages.

In particular, the processor 110 may perform the label smoothing by using the initial label of the RUS score in order to generate the RUS score label distribution. Further, the RUS score label distribution may be generated by generating adjusted RUS score labels based on the initial labels of the RUS scores of the two or more partial bone images and applying a label distribution generating logic to the adjusted RUS score label. The adjusted RUS score label may be generated by applying the adjustment logic like Equation 1 to the initial labels of the two or more RUS scores. Further, the label distribution generating logic applied to the adjusted RUS score label by the processor 110 in order to generate the label distribution may mean the Kernel function, and the Kernel function in the embodiment may be the Gaussian Kernel.

Figure 7:
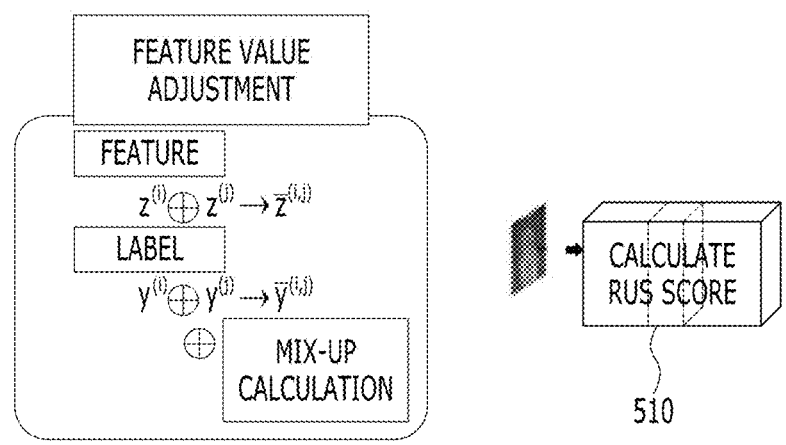
FIG. 7 is a diagram illustrating an adjustment for an initial characteristic value and a label according to the embodiment of the present disclosure.

FIG. 7 is a diagram illustrating an adjustment for an initial characteristic value and a label according to the embodiment of the present disclosure.

As described above, the partial bone RUS score estimation model 500 according to the present disclosure may perform the adjustment (particularly, the mix-up) on the initial feature value. In particular, referring to FIG. 7, the adjustment of the initial feature value may be performed in the hidden layer of the partial bone RUS score estimation model 500. The hidden layer in which the adjustment of the initial feature value is performed may be a specific value adjustment layer 510.

In order to train the partial bone RUS score estimation model 500, the processor 110 may make the adjustment (particularly, the mix-up) be performed on the initial feature value of the partial bone image 400 in the hidden layer in the operation of training the partial bone RUS score estimation model 500. The adjustment of the feature value of the partial bone image 400 may be a determination of the one or more calculated initial feature values and the adjusted feature value generated based on the predetermined (or selected) logic as an input feature value of a next layer in order to perform normalization of hidden representations of the partial bone image 400. The adjustment of the initial feature value of the partial bone image 400 may be performed by combining the initial feature values of the same type (for example, a start node and an arrival node of the transmitted feature value are the same) in the two or more partial bone images 400 for the same major point (that is, the images for the same part among the plurality of partial bone images of each of the two or more training data) by the predetermined (or selected) logic. For example, it is assumed that there are two or more partial bone images 400 for the first major point. Herein, the adjustment of the initial feature values of the partial bone images 400 in the hidden layer may be the addition of the feature values of the same type by the predetermined (or selected) logic. Herein, the predetermined (or selected) logic for adjusting the initial feature value in the hidden layer may be represented by Equation 1 below. Herein, the hyper parameter may be different from the value determined for performing the adjustment on the input layer. The adjustment of the initial feature value in the hidden layer may also occur in two or more hidden layers. The partial bone RUS score estimation model 500 may input the feature value adjusted by the predetermined (or selected) logic to a next layer.

Figure 8:
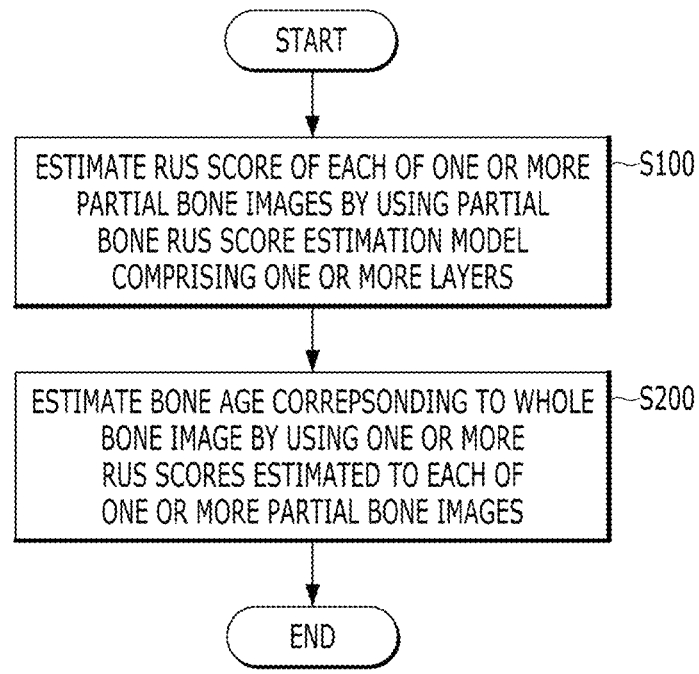
FIG. 8 is a flowchart illustrating a method of measuring bone age of a whole bone image by the processor according to an embodiment of the present disclosure.

FIG. 8 is a flowchart illustrating a method of measuring bone age of a whole bone image by the processor according to an embodiment of the present disclosure.

The processor 110 may generate one or more partial bone image from a whole bone image.

In the present disclosure, the whole bone image 200 may be the image of a body part in which bone age needs to be measured. The whole bone image 200 may include one or more major points. The one or more major points may be the points at which the RUS score 600 for measuring the bone age for the whole bone image 200 needs to be measured. That is, the processor 110 may estimate the RUS score 600 for each of the one or more major points, and calculate the whole bone age by using the one or more estimated RUS scores 600 information.

In order to measure the RUS score 600 for each of the one or more major points, the whole bone image 200 may be divided into one or more partial bone images 400. To this end, a major area extracting unit 300 may not only extract one or more major points from the whole bone image 200, but also generate the partial bone image 400 including the extracted major points.

In the present disclosure, the partial bone image 400 may be the divided part of the whole bone image 200. The partial bone image 400 may include one or more major points for measuring bone age therein. As described above, the partial bone image 400 may be generated based on the extracted major point and the size of the partial bone image 400 according to the type of extracted major point. In this case, the major point may be located at the center of the partial bone image 400.

The processor 110 according to the present disclosure may generate the partial bone image 400 from the whole bone image 200 by using the major area extracting unit 300. The processor 110 may extract one or more major points included in the whole bone image 200 by using the major area extracting unit 300, and generate one or more partial bone images 400 by using the one or more extracted major points. The major area extracting unit 300 may be established as a machine learning module trained for extracting one or more major points from the whole bone image 200. The major area extracting unit 300 may be trained so as to reduce or minimize a loss function that compares whether one or more pixels included in the whole bone image 200 correspond to one or more major points included in the whole bone image 200 with ground truth related to the major point. In particular, the major area extracting unit 300 may calculate a probability that the corresponding pixel corresponds to the major point for each of the one or more pixels included in the whole bone image 200. When the probability that the predetermined (or selected) pixel corresponds to the major point is larger than a predetermined (or selected) reference value, the major area extracting unit 300 may determine the predetermined (or selected) pixel as the major point. Further, the major area extracting unit 300 may classify the major point by type. That is, the major area extracting unit 300 may separately calculate a probability that a specific pixel corresponds to a first major point and a probability that a specific pixel corresponds to a second major point. In relation to this, the major area extracting unit 300 may generate a separate feature map for each type of major point.

The major area extracting unit 300 may generate one or more partial bone images 400 by using the extracted major point. For example, the major area extracting unit 300 may determine a size of the partial bone image 400 for each type of major point. The major area extracting unit 300 may determine a size of the partial bone image 400 by comparing the ground truth of the partial bone image area for each major point with the area of the partial bone image 400 generated by the major area extracting unit 300. In particular, the major area extracting unit 300 may be trained so as to reduce or minimize the determined loss function by using a width of a discrepancy area between the partial bone image area for each of the major points and the partial bone image 400 generated by the major area extracting unit 300. The size of the partial bone image 400 may be differently determined according to the type of major point. However, in order to reduce the amount of calculation required for the training of the major area extracting unit 300 in relation to the determination of the size of the partial bone image 400, the size of the partial bone image 400 may also be collectively determined regardless of the type of major area.

The processor 110 may estimate a RUS score for each of the one or more partial bone images by using the partial bone RUS score estimation model including one or more layers (S100).

In the present disclosure, the partial bone RUS score estimation model 500 may receive a partial bone image 400 as an input and generate the RUS score 600 of the partial bone image 400. As illustrated in FIG. 3, the partial bone RUS score estimation model 500 may exist for each of the partial bone images 400. Accordingly, the RUS score 600 may also be present for each of the one or more partial bone images 400.

The RUS score 600 is output data of the partial bone RUS score estimation model 500, so that the RUS score 600 may be generated in the one-hot encoding form of the label or the label distribution form like the training data of the partial bone RUS score estimation model 500. That is, the trained partial bone RUS score estimation model 500 may generate the RUS score 600 in the label distribution form for the partial bone image 400. In this case, the processor 110 may also determine the label in which the numerical value corresponding to the label value is highest in the label distribution generated by the partial bone RUS score estimation model 500 as the RUS score 600.

The processor 110 may estimate bone age corresponding to the whole bone image by using the one or more RUS scores estimated for each of the one or more partial bone images (S200).

The whole bone age calculation unit 700 according to the present disclosure may generate whole bone age by combining one or more RUS scores 600 generated by the one or more partial bone RUS score estimation models 500. The whole bone age calculation unit 700 may measure the whole bone age for the whole bone image 200 based on a predetermined (or selected) RUS score—bone age conversion table. In this case, the RUS score—bone age conversion table may be different depending on a gender of the whole bone image 200.

Figure 9:
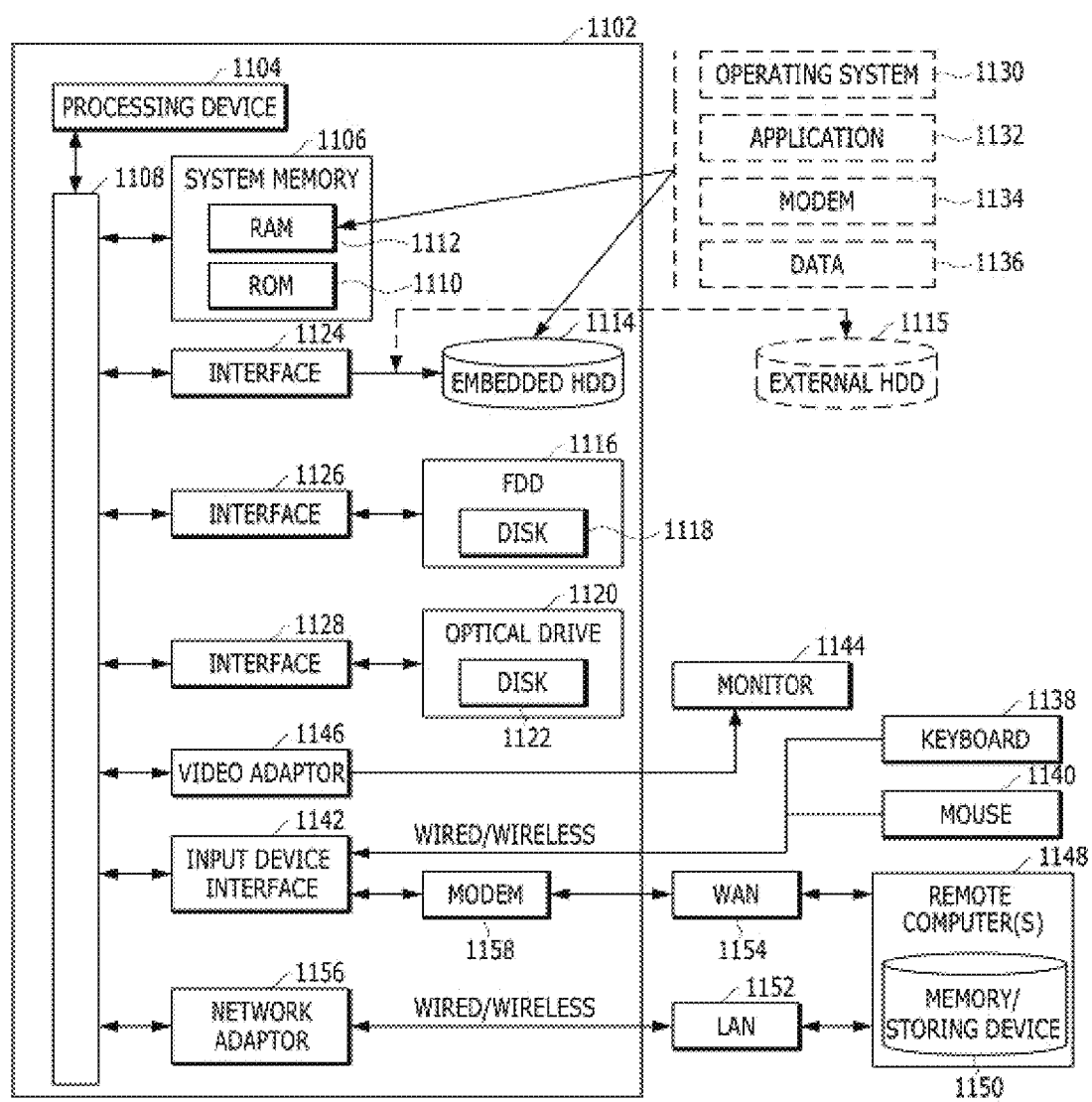
FIG. 9 is a simple and general schematic diagram illustrating an example of a computing environment in which embodiments of the present disclosure are implementable.

FIG. 9 is a simple and normal schematic view of an computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined (or selected) tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined (or selected) method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined (or selected) other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined (or selected) processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined (or selected) data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined (or selected) media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer (s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/ wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined (or selected) wireless devices or entities which are disposed and operated by the wireless communication, for example, the printer, a scanner, a desktop and/or a portable computer, a portable data assistant (PDA), a communication satellite, predetermined (or selected) equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined (or selected) technologies and techniques. For example, data, instructions, commands, information, signals, bits, symbols, and chips which may be referred in the above description may be expressed by voltages, currents, electromagnetic waves, magnetic fields or particles, optical fields or particles, or predetermined (or selected) combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined (or selected) computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A computer program stored in a non-transitory computer readable storage medium wherein the computer program comprises instructions for causing one or more processors to estimate bone age from a bone image, the instructions comprising:
estimating a RUS score for each of one or more partial bone images using a partial bone RUS score estimation model comprising one or more layers, and wherein the one or more partial bone images are generated from a whole bone image; and
estimating bone age corresponding to the whole bone image using one or more RUS scores estimated for each of the one or more partial bone images,
wherein the partial bone RUS score estimation model is trained by using a labeled partial bone image as training data, and is trained by adjusting feature values calculated from the one or more layers.

2. The computer program stored in the non-transitory computer readable storage medium according to claim 1, wherein the partial bone RUS score estimation model is trained by adjusting two or more feature values calculated from a hidden layer of the partial bone RUS score estimation model for each of two or more training data labeled with a RUS score through mix-up.

3. The computer program stored in the non-transitory computer readable storage medium according to claim 2, wherein the mix-up comprises an operation of exchanging at least a part of a first feature value corresponding to one training data calculated from the hidden layer of the partial bone RUS score estimation model with at least a part of a second feature value corresponding to other training data calculated from the hidden layer of the partial bone RUS score estimation model.

4. The computer program stored in the non-transitory computer readable storage medium according to claim 2, wherein the partial bone RUS score estimation model is trained based on a RUS score labeled on each of the two or more training data which is adjusted based on the mix-up.

5. The computer program stored in the non-transitory computer readable storage medium according to claim 4, wherein the RUS score labeled on each of the two or more training data comprises one or more classes, and wherein each of the one or more classes has an ordered correlation based on ground truth.

6. The computer program stored in the non-transitory computer readable storage medium according to claim 5, wherein the RUS score labeled on each of the two or more training data is adjusted based on a weight related to a degree of the mix-up and a calculation result for each of the one or more classes.

7. The computer program stored in the the non-transitory computer readable storage medium according to claim 5, wherein the RUS score labeled on each of the two or more training data is generated in a distribution form by performing label smoothing on a label of the RUS score.

8. The computer program stored in the non-transitory computer readable storage medium according to claim 2,
wherein a RUS score labeled on one training data is adjusted based on a weight and a calculation result of a class of the RUS score, and
wherein the weight is determined based on a degree of exchange between at least a part of a first feature value corresponding to one training data calculated from the hidden layer of the partial bone RUS score estimation model and at least a part of a second feature value corresponding to other training data calculated from the hidden layer of the partial bone RUS score estimation model.

9. The computer program stored in the non-transitory computer readable storage medium according to claim 1,
wherein the one or more partial bone images are generated based on one or more major points and a size of a partial bone image corresponding to the one or more major points,
wherein the one or more major points are determined based on a probability that each of one or more points included in the whole bone image corresponds to a major point, and
wherein the size of a partial bone image is determined based on a type of the one or more major points.

10. A computing device estimating bone age from a bone image, comprising:
a memory comprising computer executable components; and
a processor that executes the following computer executable components stored in the memory,
wherein the processor is configured to:
estimate a RUS score for each of one or more partial bone images using a partial bone RUS score estimation model comprising one or more layers, and wherein the one or more partial bone images are generated from a whole bone image; and
estimate bone age corresponding to the whole bone image using one or more RUS scores estimated for each of the one or more partial bone images,
wherein the partial bone RUS score estimation model is trained by using a labeled partial bone image as training data, and is trained by adjusting feature values calculated from the one or more layers.

11. The computing device according to claim 10, wherein the partial bone RUS score estimation model is trained by adjusting two or more feature values calculated from a hidden layer of the partial bone RUS score estimation model for each of two or more training data labeled with a RUS score through mix-up.

12. The computing device according to claim 11, wherein the mix-up comprises an operation of exchanging at least a part of a first feature value corresponding to one training data calculated from the hidden layer of the partial bone RUS score estimation model with at least a part of a second feature value corresponding to other training data calculated from the hidden layer of the partial bone RUS score estimation model.

13. The computing device according to claim 11, wherein the partial bone RUS score estimation model is trained based on a RUS score labeled on each of the two or more training data which is adjusted based on the mix-up.

14. The computing device according to claim 13, wherein the RUS score labeled on each of the two or more training data comprises one or more classes, and wherein each of the one or more classes has an ordered correlation based on ground truth.

15. The computing device according to claim 14, wherein the RUS score labeled on each of the two or more training data is adjusted based on a weight related to a degree of the mix-up and a calculation result for each of the one or more classes.

16. The computing device according to claim 14, wherein the RUS score labeled on each of the two or more training data is generated in a distribution form by performing label smoothing on a label of the RUS score.

17. The computing device according to claim 11, wherein a RUS score labeled on one training data is adjusted based on a weight and a calculation result of a class of the RUS score, and wherein the weight is determined based on a degree of exchange between at least a part of a first feature value corresponding to one training data calculated from the hidden layer of the partial bone RUS score estimation model and at least a part of a second feature value corresponding to other training data calculated from the hidden layer of the partial bone RUS score estimation model.

18. The computing device according to claim 10, wherein the one or more partial bone images are generated based on one or more major points and a size of a partial bone image corresponding to the one or more major points, wherein the one or more major points are determined based on a probability that each of one or more points included in the whole bone image corresponds to a major point, and wherein the size of a partial bone image is determined based on a type of the one or more major points.

19. A method of estimating bone age from a bone image by computing device, the method comprising:

estimating a RUS score for each of one or more partial bone images using a partial bone RUS score estimation model comprising one or more layers, and wherein the one or more partial bone images are generated from a whole bone image; and estimating bone age corresponding to the whole bone image using one or more RUS scores estimated for each of the one or more partial bone images, wherein the partial bone RUS score estimation model is trained by using a labeled partial bone image as training data, and is trained by adjusting feature values calculated from the one or more layers.

20. The method according to claim 19, wherein the partial bone RUS score estimation model is trained by adjusting two or more feature values calculated from a hidden layer of the partial bone RUS score estimation model for each of two or more training data labeled with a RUS score through mix-up.

* * * * *